(12) United States Patent
Puckett et al.

(10) Patent No.: US 9,895,245 B2
(45) Date of Patent: Feb. 20, 2018

(54) INTRODUCER SHEATH HAVING A NON-UNIFORM INNER SURFACE

(71) Applicant: Cook Medical Technologies LLC, Bloomington, IN (US)

(72) Inventors: Dean Puckett, Bloomington, IN (US); Tiffani L Cannon, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 833 days.

(21) Appl. No.: 14/196,651

(22) Filed: Mar. 4, 2014

(65) Prior Publication Data

US 2014/0257455 A1    Sep. 11, 2014

Related U.S. Application Data

(60) Provisional application No. 61/773,391, filed on Mar. 6, 2013.

(51) Int. Cl.
*A61F 2/06* (2013.01)
*A61F 2/962* (2013.01)
*A61M 25/00* (2006.01)

(52) U.S. Cl.
CPC ........... *A61F 2/962* (2013.01); *A61M 25/005* (2013.01); *A61M 25/0053* (2013.01); *A61M 25/0052* (2013.01); *A61M 2025/0047* (2013.01); *Y10T 29/49826* (2015.01); *Y10T 29/49885* (2015.01)

(58) Field of Classification Search
CPC ........... A61F 2/962; A61M 2025/0047; A61M 25/0052; A61M 25/005; A61M 25/0053; Y10T 29/49885; Y10T 29/49826
See application file for complete search history.

(56) References Cited

U.S. PATENT DOCUMENTS

| | | | |
|---|---|---|---|
| 5,380,304 A | 1/1995 | Parker | |
| 5,531,721 A | 7/1996 | Pepin et al. | |
| 5,879,342 A * | 3/1999 | Kelley | A61M 25/005 600/524 |
| 5,891,114 A | 4/1999 | Chien et al. | |
| 6,030,371 A | 2/2000 | Pursley | |
| 6,240,231 B1 | 5/2001 | Perrera et al. | |
| 6,447,488 B2 | 9/2002 | Estabrook et al. | |
| 6,554,820 B1 * | 4/2003 | Wendlandt | A61M 25/005 604/527 |

(Continued)

FOREIGN PATENT DOCUMENTS

| | | |
|---|---|---|
| EP | 0 421 650 A1 | 4/1991 |
| EP | 02 174 685 A1 | 4/2010 |

*Primary Examiner* — Richard Louis
(74) *Attorney, Agent, or Firm* — Eric D. Babych; Brinks Gilson & Lione

(57) ABSTRACT

An introducer sheath includes an elongated tubular member having a passageway extending generally longitudinally therethrough. The passageway is defined by an inner surface of the tubular member and configured to receive a medical device movably disposed therein. The introducer sheath further includes a reinforcing member engaged with the inner surface of the tubular member and extending into the passageway such that a non-uniform surface for receiving the medical device is defined thereby. The reinforcing member also has a surface therein suitable for facilitating movement of the medical device through the passageway.

8 Claims, 5 Drawing Sheets

(56) References Cited

U.S. PATENT DOCUMENTS

| | | | |
|---|---|---|---|
| 6,669,886 B1* | 12/2003 | Willard | A61M 25/005 |
| | | | 264/171.14 |
| 8,142,415 B2 | 3/2012 | Warnock, Jr. et al. | |
| 2001/0034514 A1 | 10/2001 | Parker | |
| 2002/0045929 A1* | 4/2002 | Diaz | A61F 2/95 |
| | | | 623/1.11 |
| 2002/0111590 A1* | 8/2002 | Davila | A61B 17/0644 |
| | | | 604/265 |
| 2004/0193179 A1* | 9/2004 | Nikolchev | A61B 17/12022 |
| | | | 606/108 |
| 2005/0090890 A1 | 4/2005 | Wu | |
| 2006/0074478 A1* | 4/2006 | Feller, III | A61B 17/12022 |
| | | | 623/1.11 |
| 2007/0112407 A1 | 5/2007 | Mertens | |
| 2009/0240235 A1 | 9/2009 | Murata | |
| 2010/0145429 A1 | 6/2010 | Dhoke et al. | |

\* cited by examiner

INTRODUCER SHEATH HAVING A NON-UNIFORM INNER SURFACE

This application claims priority to U.S. Provisional Application No. 61/773,391, filed Mar. 6, 2013, which is hereby incorporated by reference herein.

BACKGROUND

1. Technical Field

The present invention relates generally to medical devices and, in particular, to an introducer sheath and, more particularly, to an introducer sheath having a non-uniform inner surface.

2. Background Information

Introducer sheaths are widely used for delivering an implantable medical device such as a stent to a deployment site within the vasculature of a patient. Deployment of stents and other expandable medical interventional devices is now a routine practice, and such deployment is often carried out with only a minimum of complications, if any. This is particularly true when such devices have a relatively short length (e.g., less than about 80 mm) and/or a relatively modest outer diameter. However, as medical technology has progressed, stents and other interventional devices having longer lengths (e.g., about 100 to 300 mm or more) and/or having outer coatings, coverings, etc., that increase the effective outer diameter of the stent have become more common. When such stents are placed in a sheath lumen for delivery to the target site, the greater length and/or outer diameter of the stent increases the frictional forces between the sheath and the stent thereby increasing deployment forces necessary to extract the stent from the sheath when compared to shorter and/or lesser diameter stents.

One way of decreasing frictional forces during deployment of a stent is by having fewer contacts points between the stent and the inner surface of the introducer sheath. For example, U.S. Pat. Publication No. 2010/0145429, the entire contents of which is hereby incorporated by reference, describes introducer sheaths having a non-uniform inner surface to create fewer points of contact. While the introducer sheaths described by U.S. Pat. Publication No. 2010/0145429 have reduced friction between the sheath and the stent, it is desired to provide further improved introducer sheaths that have reduced contact points between the stent and the sheath.

SUMMARY

The problems of the prior art are addressed by the introducer sheath of the present invention. In one form thereof, the introducer sheath includes an elongated tubular member having a passageway extending generally longitudinally therethrough. The passageway is defined by an inner surface of the tubular member and configured to receive a medical device movably disposed therein. The introducer sheath can further include a reinforcing member comprising a coating engaged with the inner surface of the tubular member and extending into the passageway such that a non-uniform surface for receiving the medical device is defined thereby.

In another form thereof, the introducer sheath includes an elongated tubular member having a passageway extending generally longitudinally therethrough. The passageway is defined by an inner surface of the tubular member and configured to receive a medical device movably disposed therein. The introducer sheath also includes a reinforcing member engaged with the inner surface of the tubular member and extending into the passageway such that a non-uniform surface for receiving the medical device is defined thereby. The reinforcing member also has a surface therein suitable for facilitating movement of the medical device through the passageway.

In still another form thereof, the invention comprises a method for forming an introducer sheath. A reinforcing member is positioned over a mandrel, and an elongated tubular member is positioned over the reinforcing member and the mandrel. The tubular member has a passageway extending generally longitudinally therethrough. The passageway is defined by an inner surface of the tubular member and configured to receive a medical device movably disposed therein. The tubular member is heated to a temperature sufficient to engage the reinforcing member with the inner surface of the tubular member. The reinforcing member extends into the passageway such that a non-uniform surface for receiving the medical device is defined thereby. The reinforcing member also has a surface therein suitable for facilitating movement of the medical device through the passageway.

BRIEF DESCRIPTION OF THE DRAWINGS

The invention may be more fully understood by reading the following description in conjunction with the drawings, in which.

DETAILED DESCRIPTION

Figure 1:
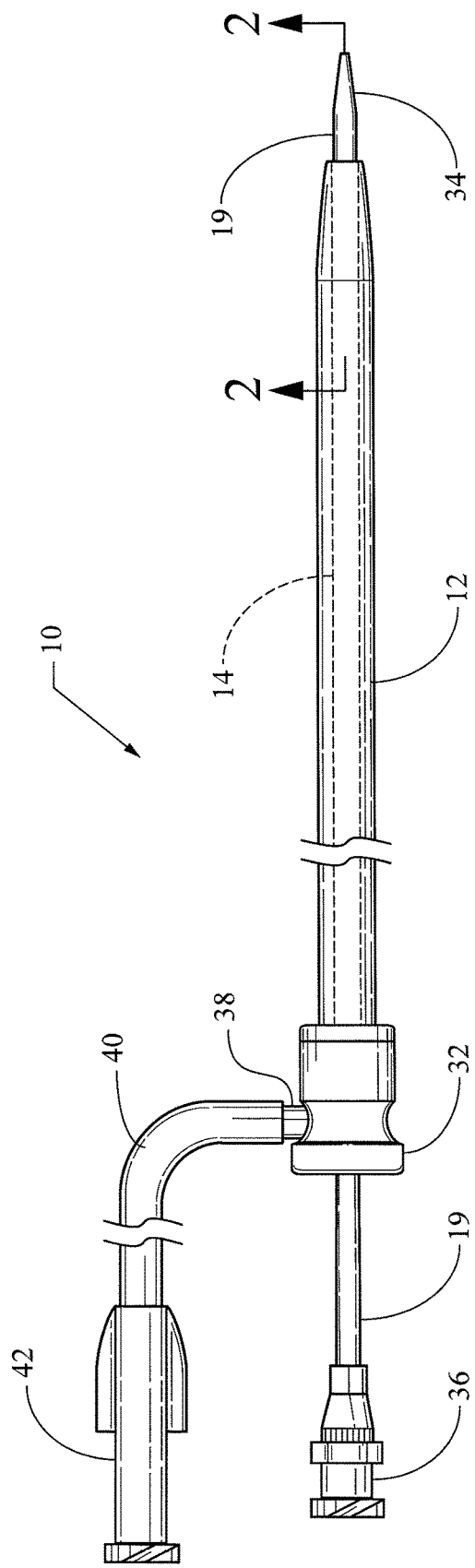
FIG. 1 is a side view of an introducer sheath according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the sheath, as well as the axial ends of component features of the sheath. The term "proximal" is used in its conventional sense to refer to the end of the sheath (or component thereof) that is closest to the operator during use of the device. The term "distal" is used in its conventional sense to refer to the end of the sheath (or component thereof) that is initially inserted into the patient, or that is closest to the patient during use.

When conventional introducer sheaths are used to deploy medical interventional devices, such as stents, having a relatively short length, such deployments may often be carried out without undue complication. Typically, the stent is nested, or housed, in the distal portion of the sheath in a radially compressed condition. As the stent is deployed from the distal end of the sheath, the stent radially expands to the diameter of the body passageway in which it has been positioned. The relatively short length of the stent, most of which are less than about 80 mm in length, typically provides minimal resistance to the interior of the sheath as the compressed sheath is deployed therefrom.

When comparatively longer stents (e.g., stents greater than about 100 mm in length, and especially, stents greater than about 140 mm in length) are deployed from prior art sheaths, however, the deployment of the stent from a sheath may be less than optimal. Due to the greater length of these stents, a greater aggregate frictional force is created between the compressed stent and the interior wall of the sheath, when compared to the frictional forces created by a stent of a lesser length. As a result, a higher push force must typically be imparted by the inner catheter to overcome the tendency of the stent to remain with the sheath as the sheath is withdrawn from the passageway. A high push force as described may also be required upon deployment of coated or covered stents of any length from the sheath. This is due to the increased frictional forces between the wall of the sheath and the larger diameter coated or covered stent when compared to an otherwise similar, but uncoated or uncovered stent.

The frictional forces between the compressed stent and the interior wall of the sheath during deployment may cause the sheath to stretch, or elongate, in the longitudinal direction as the sheath is withdrawn from around the stent. Stretching may have little practical significance when smaller stents are positioned within the sheath. However, such stretching can become problematic with larger stents and/or with coated or covered stents, such that in some cases, the stent cannot be efficiently deployed from the elongated sheath.

One way to address the problem of elongation of the sheath is to increase the stiffness of the outer jacket material of the sheath. A sheath having a stiffer outer jacket has less propensity to stretch upon deployment of the stent when compared to one having a more flexible outer jacket. As a result, the likelihood of deployment difficulties is minimized. Another way to address the problem of elongation of the sheath is to have an inner surface of the sheath have a non-uniform surface so that the stent contacts the inner surface in fewer locations than an inner surface that is uniform or smooth. Described herein are sheaths that include a reinforcing member that can both stiffen the outer jacket while also providing a non-uniform inner surface for the sheath.

In FIG. 1, a sheath 10 is shown in combination with an optional dilator, or inner catheter, 19 and a connector hub 32. Dilators, inner catheters, and connector hubs for use with introducer devices, such as the sheath 10, are well known in the art, and the elements illustrated in FIG. 1 may be replaced with various other elements known in the art. As shown herein, inner catheter 19 extends longitudinally through the passageway of the sheath 10. The inner catheter 19 includes a tapered distal end 34 for accessing and dilating an access site, typically over a wire guide 21 (shown in FIG. 2), by any conventional access technique, such as the well-known Seldinger technique. A Luer lock connector 36 may be attached at the proximal end of the inner catheter 19 for connection to a syringe or other medical apparatus in well-known fashion.

Optional connector hub 32 is attached about the proximal end of the sheath 10 during use. Connector hub 32 may include one or more conventional valve members, such as disk valves (not shown), for preventing the backflow of fluids therethrough. Connector hub 32 may also include a side arm 38, to which a polymeric tube 40 and a conventional connector 42 may be connected for introducing and aspirating fluids therethrough in well-known fashion.

Figure 2:
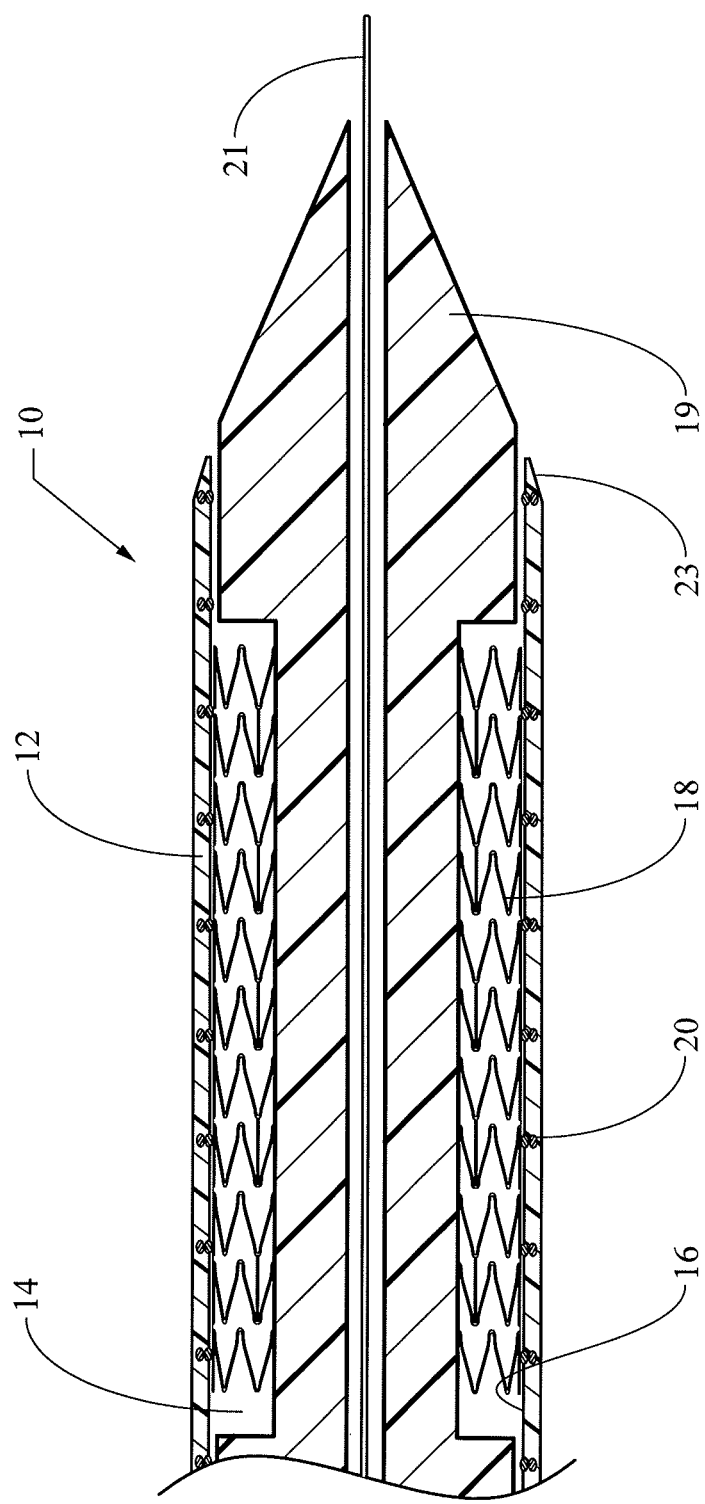
FIG. 2 is a longitudinal cross-sectional view of a segment of the introducer sheath, taken along line 2-2 of FIG. 1.
Figure 3:
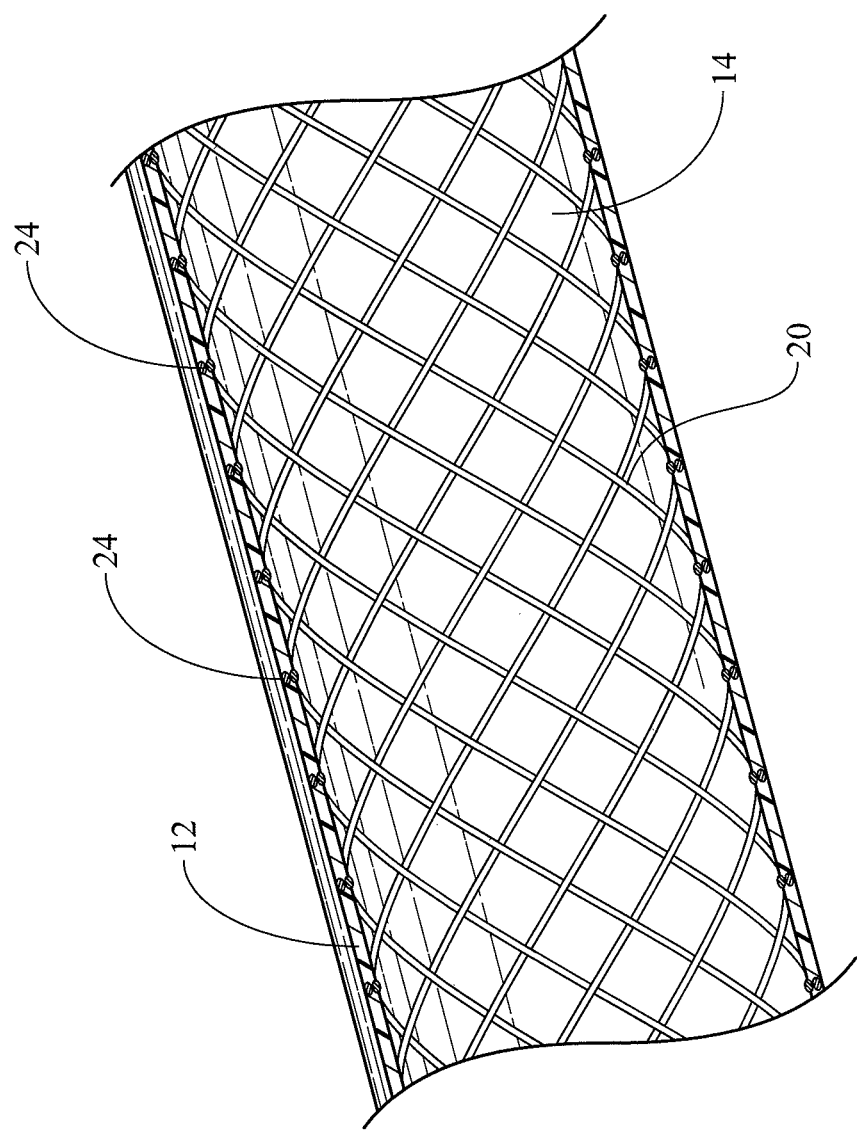
FIG. 3 is a cross-sectional perspective view of a segment of the introducer sheath, taken along line 2-2 of FIG. 1.

FIG. 2 is an enlarged longitudinal cross-sectional view of a segment of the distal end of the introducer sheath 10 of FIG. 1, and FIG. 3 is a perspective view of a cross-section of the introducer sheath 10 of FIG. 1. In particular, FIGS. 2 and 3 illustrate the structure of the sheath wall. The introducer sheath 10 includes an elongated tubular member 12 having a passageway 14 extending generally longitudinally therethrough. The passageway 14 is defined by an inner surface 16 of the tubular member 12 and is configured to receive a medical device 18 movably disposed therein.

The passageway 14 is configured to maintain the medical device 18, such as a stent, in a compressed configuration for delivery to a deployment site within the body of the patient. The stent may be self-expanding or balloon-expandable, and may be deployed according to conventional methodology, such by an inflatable balloon catheter, by a self-deployment mechanism (after release from a catheter), or by other appropriate means. Preferred materials include those materials that can provide the desired functional characteristics with respect to mechanical load bearing, biological compatibility, modulus of elasticity, or other desired properties. The stent can include, for example, a metallic material or alloy selected from stainless steel, nickel, silver, platinum, palladium, gold, titanium, tantalum, iridium, tungsten, cobalt, chromium, a molybdenum alloy, a molybdenum alloy including about 0.4% to about 0.8% of lanthanum oxide ($Li_2O_3$), a nickel-titanium alloy, or a superelastic nickel-titanium (NiTi) alloy. The stent may be any suitable vascular stent such as the commercially available Gianturco-Roubin FLEX-STENT®, GRII™, SUPRA-G, ZILVER, or V FLEX coronary stents from Cook Medical (Bloomington, Ind.).

The medical device 18 is disposed within the distal portion of the introducer sheath 10 and is supported by an inner catheter 19, or a pusher member. The inner catheter 19 is slideably positioned within the passageway 14 of the introducer sheath 10. During deployment, the inner catheter 19 maintains the longitudinal position of the medical device 18 as the introducer sheath 10 is withdrawn to expose the medical device 18 from the distal end of the introducer sheath 12. The introducer sheath 12 may be introduced over a wire guide 21. The wire guide 21 is inserted in the vessel with an introducer needle using, for example, the well-known percutaneous vascular access Seldinger technique. Furthermore, the introducer sheath 10 may have a tipped distal end 23 to more easily insert the introducer sheath 12 into the vessel. The distal end 23 can also include a radiopaque material in order to see the location of the distal end 23 within the vessel.

As shown in FIGS. 2 and 3, the distal portion of the introducer sheath 10 includes a non-uniform surface in the passageway 14. As will be discussed in further detail below, the non-uniform surface is configured to reduce contact between the outer surface of the medical device 18 and the inner surface 16 of the passageway 14.

The introducer sheath 10 includes a reinforcing member 20 engaged with the inner surface 16 of the tubular member 12. For example, the reinforcing member 20 can be coupled to or embedded into the inner surface 16 of the tubular member 12. The reinforcing member 20 extends into the passageway 14 such that a non-uniform surface for receiving the medical device 18 is defined thereby. The non-uniform surface can allow the medical device 18 to be moved through the passageway 14 with less force since the medical device 18 contacts less area along the passageway 14 of the introducer sheath 10 than a uniform or smooth surface. The reinforcing member 20 can extend the entire length of the introducer sheath 10 or can extend a segment of the length. In the example shown, the reinforcing member 20 can be positioned such that the reinforcing member 20 only resides in the distal region of the introducer sheath 10 where the medical device 18 is positioned within the passageway 14.

Figure 4:
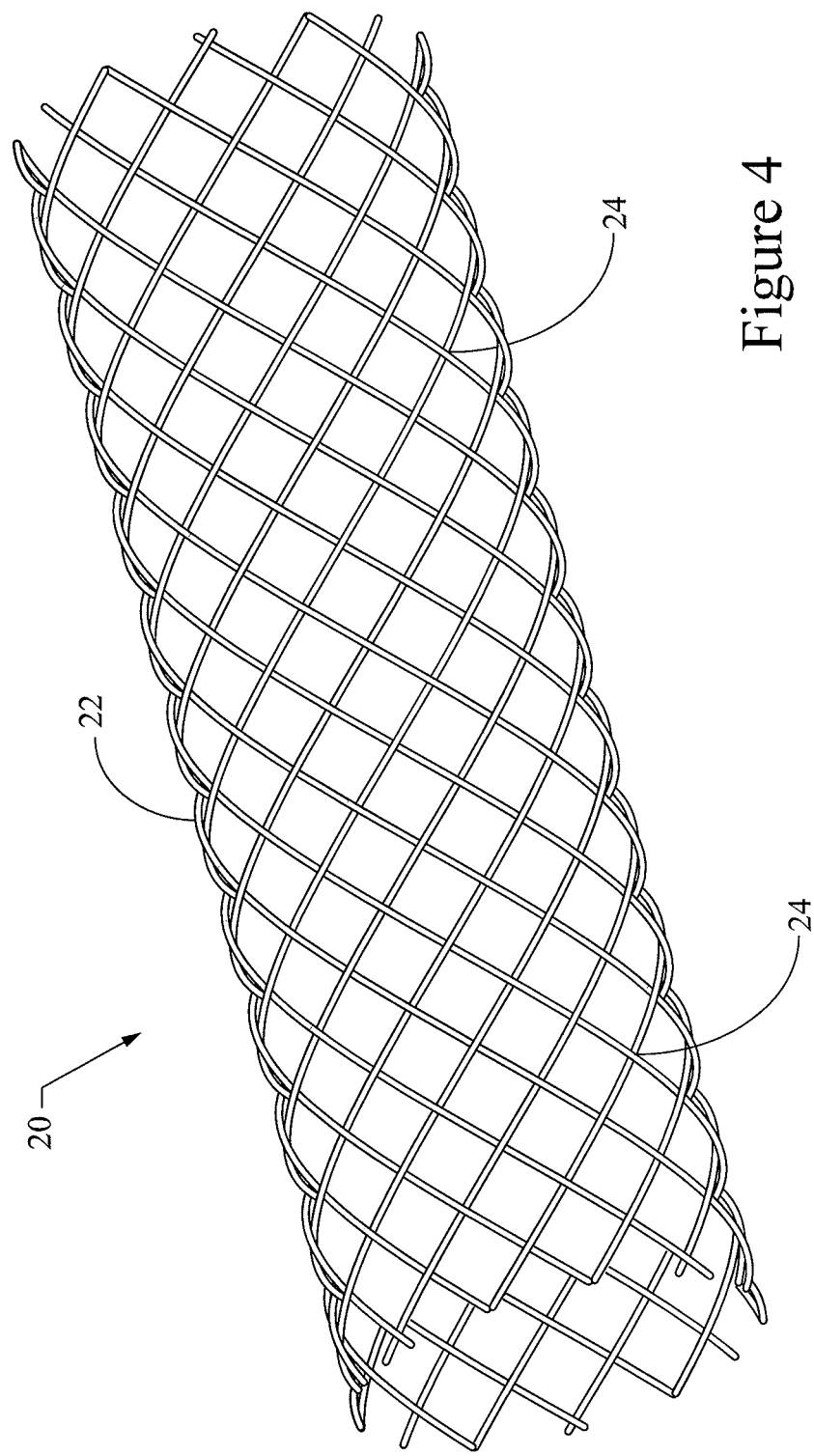
FIG. 4 is a perspective view of the reinforcing member of the introducer sheath of FIG. 1.

FIG. 4 illustrates a perspective view of the reinforcing member 20 illustrated in FIGS. 2 and 3. The reinforcing member 20 can have a tubular shape similar to that of the tubular member 12. The reinforcing member 20 is illustrated as a braid, but other configurations are possible such as a coil, weave, mesh, etc. The reinforcing member 20 can be formed from one or more wires to form, for example, the braid. For instance, the braid can be formed from a plurality of wires 22 that form cross-over points 24 where a wire is adjacent to another wire. The cross-section side view of FIG. 2 is through cross-over points 24 of the braid, and the cross-section perspective view of FIG. 3 is also through cross-over points 24 of the braid. Since two wires are adjacent to one another at the cross-over points 24, the braid has a greater effective wall thickness at the cross-over points 24 than other regions of the braid. For example, the wires 22 can have a diameter of about 10 μm to about 100 μm. As shown in FIG. 4, the braid can have a relatively open structure in regions between cross-over points 24 that result in openings extending through the tubular wall. For example, each cross-over points 24 may be spaced from a closest neighboring cross-over point 24 between about 500 μm and about 5 mm. To better illustrate the braid structure in FIG. 4, a back portion of the tubular wall is hidden by a front portion of the tubular wall; however, the back portion of the real braid would actually be able to be seen though the opening between the wires of the braid.

As described above, the reinforcing member 20 can be at least partially embedded within the tubular member 12 while at least some of the reinforcing member 20 is exposed or otherwise protrudes in the passage 14. For example, at least about 90% of a thickness or a volume of the reinforcing member 20 can be embedded within the tubular member 12, or between about 90% and about 99% of a thickness or a volume of the reinforcing member 20 can be embedded within the tubular member 12. When the reinforcing member 20 is a braid or otherwise has cross-over points 24, the cross-over points 24 can be partially exposed on the inner surface 16 of the tubular member 12 while portions of the reinforcing member 20 that do not form cross-over points 24 can be completely embedded within the tubular member 12.

As described above, the distal portion of the sheath 10 includes a non-uniform surface in the passage 14. The non-uniform surface provides advantages during the actual deployment of the medical device 18 from the introducer sheath 10 by promoting less surface contact between the inner surface 16 of the tubular member 12 and the medical device 18. For example, the reinforcing member 20 can support the medical device 18, and the medical device may not contact or at least not substantially contact the inner surface 16 of the tubular member 12 (e.g., the inner surface 16 of the tubular member does not support the medical device 18). As illustrated in FIG. 2, the reinforcing member 20 can result in a space or gap formed between the medical device 18 and the inner surface 16 of the tubular member 12.

The size and configuration of the non-uniform surface can be based on the size of the medical device 18 which will be deployed within the body of the patient. As such, the non-uniform surface can encompass multiple configurations.

The reinforcing member 20 can have a surface suitable for facilitating movement of the medical device 18 through the passageway 14. For example, typical reinforcing members that are for reinforcing a sheath that are completely embedded within a sheath or are on the outer surface of the sheath are often steel or other metal alloys. Although a metal or a metal alloy may be used as the reinforcing member 20, the coefficient of friction between a metal alloy and a medical device can be large enough that that medical device may be difficult to move through a passage. Therefore, the reinforcing member 20 can have a coating comprising a first material. The first material may be a lubricious material to provide a slippery surface to allow the medical device 18 more easily move through the passageway 14. The first material can have a coefficient of friction lower than that of a metal or metal alloy of a type commonly used for forming a braid such as stainless steel or nitinol. For example, the first material can include a polymer such as a poly-fluorocarbon (e.g., tetrafluoroethylene, fluorinated ethylene propylene, or perfluoroalkoxy) or other lubricious polymers or blends thereof. Additional examples of the first material include a hydrophilic material, silicone, diamond or diamond-like material, Nedox®, etc. The coefficient of friction between the reinforcing member 20 and the medical device 18 can be less than about 0.20. In one example, the reinforcing member 20 can include a core coated with the first material. The core can be or include a metal such as iron, tungsten, platinum, cobalt, chrome, nickel, etc. or include a metal alloy such as stainless steel, nitinol, etc.

The reinforcing member 20 can be formed by having wires coated with the first material and then formed into the reinforcing member 20 (e.g., braid). Alternatively, the reinforcing member 20 can be formed first and then the reinforcing member 20 can be coated with the first material. The coating can be, for example, between about 5 μm and about 50 μm. The first material can be coated onto the reinforcing member 20 by various methods such as spray coating or dip coating. Furthermore, the first material may be selectively applied to certain regions of the reinforcing member 20. For example, the first material may only be applied to surfaces of the reinforcing member 20 that will be exposed within the passageway 14. For instance, an inner surface of a tubular braid may be coated with the first material while the outer surface of the tubular braid is not coated with the first material. Depending on materials selected, by not coating the outer surface with first material, the reinforcing member 20 can form a stronger bond with the tubular member 12 than if the outer surface was coated with the first material.

The reinforcing member 20 can include wires 22 that have a circular cross-sectional shape, as shown in FIG. 4, or the wires 22 can have other cross-sectional shapes such as square, rectangular, oval, etc. Furthermore, the wires 22 can be flat. When the wires 22 are flat or non-circular, the first material can be coated onto one side of the wires 22 while the opposite side is not coated with the first material. The wires 22 can then be formed into the reinforcing member 20. Since the wires 22 are flat or non-circular, during the forming process such as braiding, the wires 22 can be manipulated so that the side that is coated with the first material forms the inner surface of the reinforcing member 20 and the side that is not coated with the first material forms the outer surface of the reinforcing member 20.

The reinforcing member 20 need not necessarily have a metal or metal alloy core. For example, the reinforcing member 20 can consist essentially of the first material. As such, the reinforcing member 20 may not have a coating. For example, the reinforcing member 20 can be formed from polymer (e.g., poly-fluorocarbon) wires. The polymer wire can be both lubricious and provide reinforcement such as polyimide, polypropylene, polyether ether ketone, polyether block amide, polyurethane, or a combination thereof.

Figure 5:
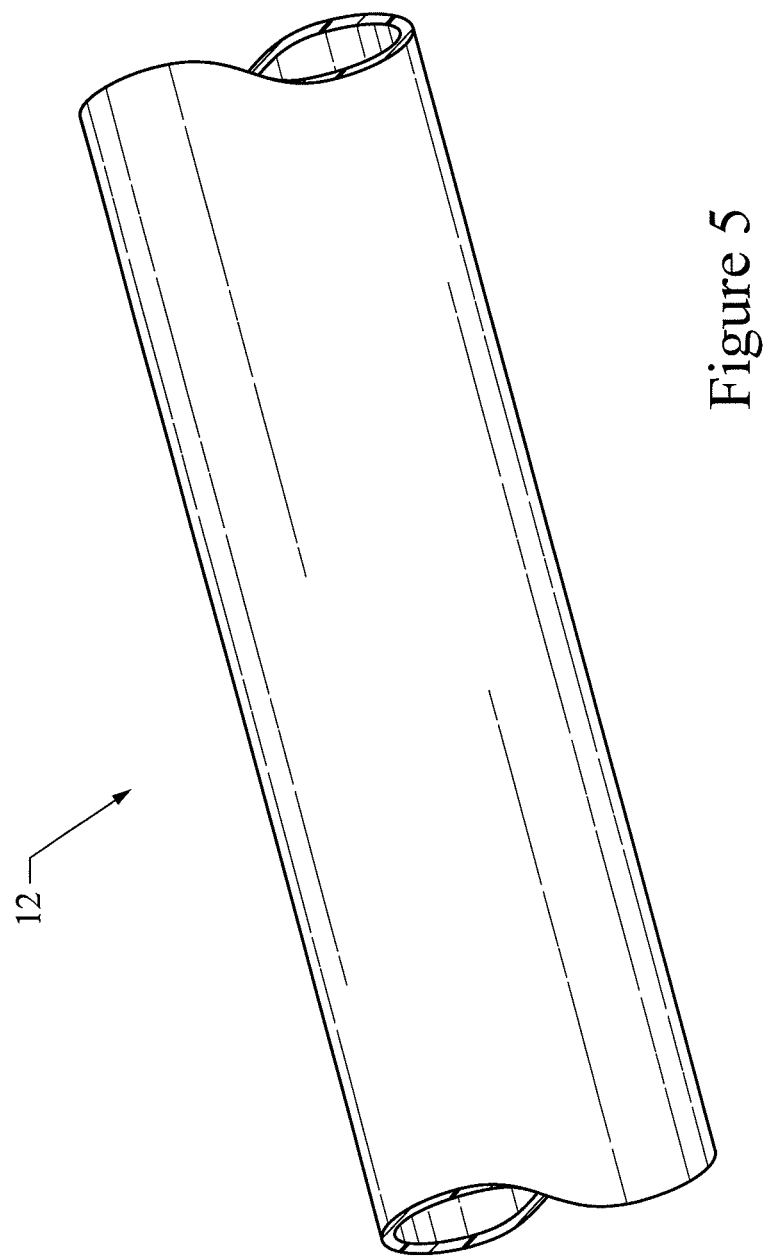
FIG. 5 is a perspective view of a section of the tubular member of the introducer sheath of FIG. 1.

As described above, the reinforcing member 20 can be partially embedded within the tubular member 12. As such, the tubular member 12 can be formed of a material capable of engaging the reinforcing member 20. For example, the tubular member 12 can be a second material comprising a polymer such as a polyamide (e.g., nylon), polyether block amide, tetrafluoroethylene, polyurethane, polypropylene, or a combination thereof. FIG. 5 is a perspective view of a section of the tubular member 12 shown in FIG. 2. The wall thickness of tubular member 12 can vary depending on a particular application, and for example, the wall thickness can be about 50 μm to about 1 mm. The tubular member 12 may be a single layer or have more than one layer. For example, an inner most layer can be a material having a low coefficient of friction such as a poly-fluorocarbon or other material described above with regard to reinforcing member 20. Alternatively, the tubular member 12 may be a single material having a low coefficient of friction. However, the tubular member 12 does not necessarily need to have low coefficient of friction since the medical device 18 can be supported by the reinforcing member 20 and not the tubular member 12. Therefore, the second material can have a coefficient of friction equal to or greater than the coefficient of friction of the first material of the reinforcing member 20.

The introducer sheath 10 can be manufactured by a various methods. In one example, a method can include positioning the reinforcing member 20 over a mandrel. The mandrel can have a cylindrical shape where the mandrel can be configured to extend through a passage of the reinforcing member 20. After the reinforcing member 20 is positioned over the mandrel, the tubular member 12 can be positioned over the reinforcing member 20 and the mandrel. As such, the mandrel can be sized to fit within the passageway of a tubular member 12.

The assembly comprising the mandrel, the reinforcing member 20, and the tubular member 12 can be positioned within a suitable heat shrink enclosure. The entire assembly can then be heated to a temperature sufficient to engage the reinforcing member 20 with the inner surface 16 of the tubular member 12. For example, the heating of the tubular member 12 can include heat shrinking the tubular member 12 onto the mandrel. For instance, depending on particular material, the tubular member may be heated to about 80° C. to about 200° C. The reinforcing member 20 may be at least partially embedded within the tubular member 12 as a result of the heating of the tubular member 12. After the tubular member 12 is shrunk onto the mandrel and cooled, the heat shrink material is removed, and the tubular member 12 with the reinforcing member 20 can be removed from the mandrel. The resulting introducer sheath 10 can result in the reinforcing member 20 extending into the passageway 14 such that a non-uniform surface is defined for receiving the medical device 20 movably disposed therein. Furthermore, as described above, the reinforcing member 20 can have a surface for facilitating movement of the medical device through the passageway 14.

Additional details of the construction or composition of the various elements of sheath 10 not otherwise disclosed are not believed to be critical to the present invention, so long as the recited elements possess the strength and/or physical properties to enable them to perform as required. Many such details not described herein are recited in detail in U.S. Pat. No. 5,380,304, U.S. Patent Publication No. 2001/0034514, and U.S. Patent Publication No. 2010/0145429, the entire contents of each of which is hereby incorporated by reference.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. An introducer sheath comprising:
    an elongated tubular member having a passageway extending generally longitudinally therethrough, the passageway being defined by an inner surface of the tubular member and configured to receive a medical device movably disposed therein; and
    a reinforcing member comprising a coating engaged with the inner surface of the tubular member and extending into the passageway such that a non-uniform surface for receiving the medical device is defined thereby,
    wherein the reinforcing member comprises a braid, and wherein the braid comprises wires, the wires of the braid form cross-over points, the cross-over points being partially exposed on the inner surface of the tubular member and portions of the braid that do not form cross-over points being completely embedded within in the tubular member.

2. The introducer sheath of claim 1, wherein the coating comprises a lubricious material.

3. The introducer sheath of claim 1, wherein the coating comprises poly-fluorocarbon.

4. The introducer sheath of claim 1, wherein the reinforcing member comprises a metal or metal alloy core.

5. The introducer sheath of claim 1, in combination with a medical device disposed within the passage of the tubular member and axially supported by the reinforcing member.

6. The introducer sheath of claim 1, wherein the reinforcing member consists essentially of a polymer.

7. The introducer sheath of claim 5, wherein the medical device comprises a stent.

8. The introducer sheath of claim 5, wherein a coefficient of friction between the reinforcing member and the medical device is less than about 0.20.

* * * * *